United States Patent [19]

Wiles

[11] Patent Number: Plant 6,634

[45] Date of Patent: Feb. 28, 1989

[54] ACHIMENES PLANT NAMED WHITE ROSE

[75] Inventor: Linda S. Wiles, Greenwood, S.C.

[73] Assignee: Geo. W. Park Seed Co., Inc., Greenwood, S.C.

[21] Appl. No.: 103,033

[22] Filed: Sep. 30, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An Achimenes plant named White Rose.

2 Drawing Sheets

1

The present invention comprises a new and distinct cultivar of Achimenes plant, hereinafter referred to by the cultivar name White Rose.

White Rose is a product of a planned breeding program which had the objective of creating new Achimenes cultivars having superior vigor, good branching habits, suitability for pot plants or hanging baskets, double flowers 2" or more in diameter and of various colors, early-flowering, floriferousness, and a long flowering season. Such traits in combination were not present or needed improvement in previously available commercial cultivars of this type.

White Rose was originated from a hybridization made in a controlled breeding program in Greenwood, S.C. in 1984. Both the male and female parent were identified by the breeding number 840942-2, with the female parent being selfed from the male parent.

White Rose was discovered and selected as one flowering plant within the progeny of the stated parentage by Linda Saussy Wiles on Aug. 21, 1985, in a controlled greenhouse environment in Greenwood, S.C.

Asexual reproduction of the new cultivar by rhizomes, as performed initially by Linda Saussy Wiles at Greenwood, S.C. has demonstrated that the combination of characteristics as herein disclosed for White Rose are firmly fixed through successive generations of asexual reproduction.

White Rose has not been observed under all possible environmental conditions. The phenotype may vary significantly with variations in environment such as temperature, light intensity, and day length. The following observations, measurements, and comparisons describe plants grown in Greenwood, S.C. under greenhouse conditions which approximate those generally used in commercial practice.

The following traits have been repeatedly observed and are determined to be basic characteristics of White Rose, which in combination distinguish this Achimenes as a new and distinct cultivar:

(1) The flowers are double in form and $1\frac{3}{4}$" to $2\frac{1}{2}$" in diameter. There are five (5) full size petals and 6 to 8 or more smaller petals measuring 1.0"×1.0" or more when fully expanded.

(2) The upper surface flower color of the outer petals is an attractive white, with the petals showing silver white on the reverse or underside. Under stress conditions, double petals may retract somewhat into the throat showing HCC 663/3 Chartreuse Green, with some lines and dots of HCC 931/1×834/1 Purple also being apparent.

2

(3) Generally, two to three flowers appear at each node. Plants are erect when young, and semi-trailing towards end of growing season.

(4) Rhizomes start growing early, producing plants rapidly. From rhizomes planted in early April, flowering plants were available by mid-June.

(5) Plants continue to flower well into late November.

(6) Highly floriferous flowering habit.

Of the many commercial cultivars known to the present inventor, the most similar in comparison to White Rose is Blue Rose, disclosed in U.S. Plant Pat. No. 5,919. Reference is made to attached Chart A which compares certain characteristics of White Rose to those same characteristics of Blue Rose.

The accompanying color photographic drawings show typical inflorescence and foliage characteristics of White Rose, with the colors being as nearly true as possible with illustrations of this type. Sheet 1 is a perspective view of the plant, and sheet 2 comprises a greatly enlarged photo of a single flower and surrounding foliage.

In the following description, color references are made to the Horticultural Color Chart (HCC), or to The Royal Horticultural Society Colour Chart (R.H.S.) where indicated. The color values were determined between 11:30 am. and 12:30 pm. on Sept. 24, 1986 under 2300 foot candles of light intensity at Greenwood, S.C.

Classification:

A. *Botanical.*—Achimenes hybrid., cv. White Rose.

B. *Commercial.*—Achimenes.

PLANT

A. General appearance:

*Height.*—Erect when young; semi-trailing later.

*Growth.*—Bushy.

*Internode.*—Distance $\frac{3}{4}$"–$1\frac{5}{8}$" (1.9 cm to 4.1 cm).

B. Foliage:

*Leaves.*—Numerous.

*Shape.*—15/16"×$1\frac{3}{4}$" to $1\frac{1}{8}$"×$2\frac{1}{4}$" (2.4 cm by 4.4 cm to 2.9 cm by 5.7 cm).

*Appearance.*—Serrated.

*Color.*—Top side Parsley Green HCC 0962. Bottom side Pod Green-Parsley Green HCC 061/3×0962/3.

*Texture.*—Pubescent on both upper and lower surfaces.

C. Flowers:

*Borne.*—2–3 flowers per node at most nodes.

*Type of stems.*—Short.

*Number of flowers per stem.*—One.

*Quantity of blooms.*—Abundant.

D. Blooms:

*Size.*—1¾" to 2½" (4.4 cm to 6.4 cm).

*Petalage.*—Double, five (5) full size outer petals, 6–8 or more smaller inner petals.

*Shape.*—Approximately round.

*Color.*—Outside petals, upper surface white, under surface silver white. Inner petals, upper surface white, occasionally with very faint pink-white cast at center. If inner petals retract then HCC 663/1 Chartreuse Green is partially visible with Purple HCC 931/1×834/1 lines and dots visible.

E. Reproductive organs:

*Stamens.*—0–5, usually staminode.

*Filaments.*—4–5, usually attached to petals.

*Anthers.*—Very rare, 0–4.

*Pollen.*—None.

*Pistils.*—One.

*Styles.*—1, very reduced and deformed.

*Seed.*—Will not normally produce seed.

Disease resistance: No known disease problems on plants.

CHART A

| CHARACTERISTIC | BLUE ROSE | WHITE ROSE |
|---|---|---|
| Flower size | 1.7–2.0" | 1.8–2.5" |
| Smaller petals | 4–6, 0.6" by 0.6" | 6–8, 1.0 × 1.0" |
| Leaf size | 1.0" × 1.7–2.5" | 0.9 × 1.8 to 2.1" × 2.3" |
| Leaf color | HCC 0962 Parsley Green, with HCC 061/3 Pod Green reverse | HCC 0962 Parsley Green, with HCC 061/3 × 0962/3 Pod Green - Parsley Green reverse |
| Internode spacing | 0.7"–1.2" | 0.8"–1.6" |
| Stamens | 0–4 | 0–5, usually staminode |
| Filaments | 4, sometimes attached to petals | 4–5, usually attached to petals |
| Anthers | variable 0–4 | very rare 0–4 |
| Pollen | some on occasion | none |
| Pistils | 1 | 1 |
| Styles | 1, normal | 1, reduced and deformed |
| Flower color | HHC 40/2 Hyacinth Blue, with Silver White reverse; if inner petals retract, HCC 601/3 Primrose Yellow and HCC 28 Fuschia Purple lines are visible in throat | White, occasionally with a very faint Pink-White cast at the center, with Silver White reverse; if inner petals retract, HCC 663/1 Chartreuse Green and HCC 931/1 × 834/1 are visible in throat |

I claim:

1. A new and distinct cultivar of Achimenes plant named White Rose, as illustrated and described.

* * * * *

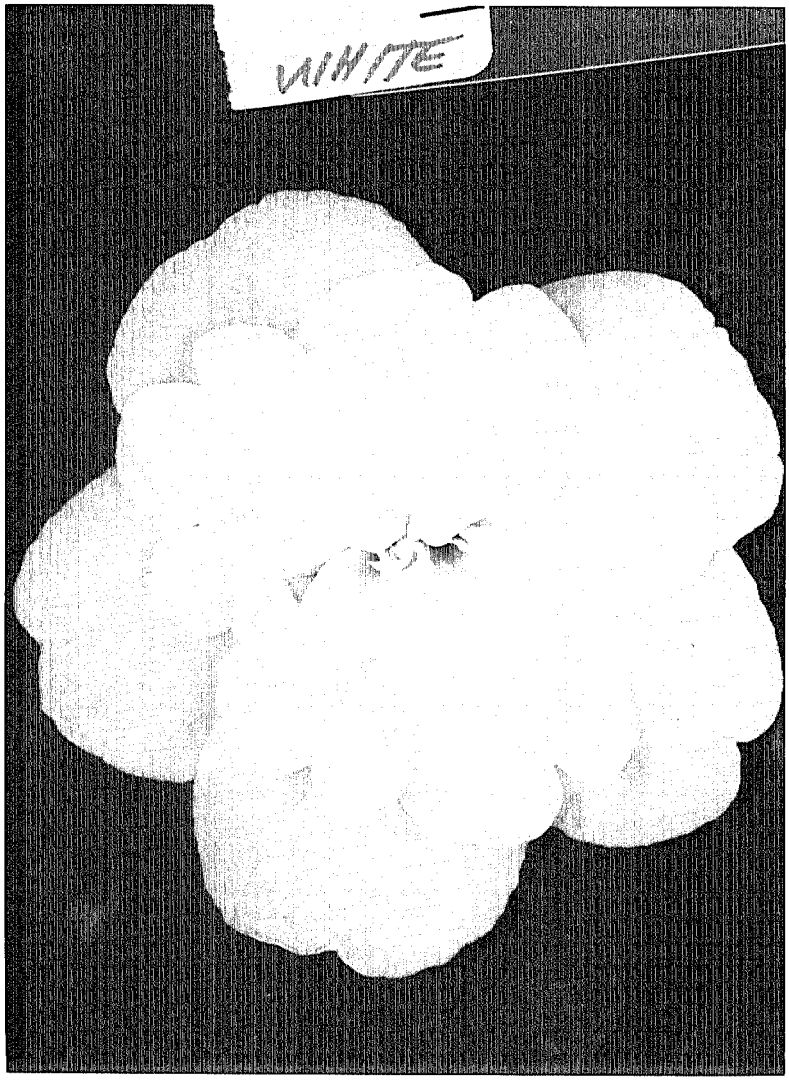
WHITE

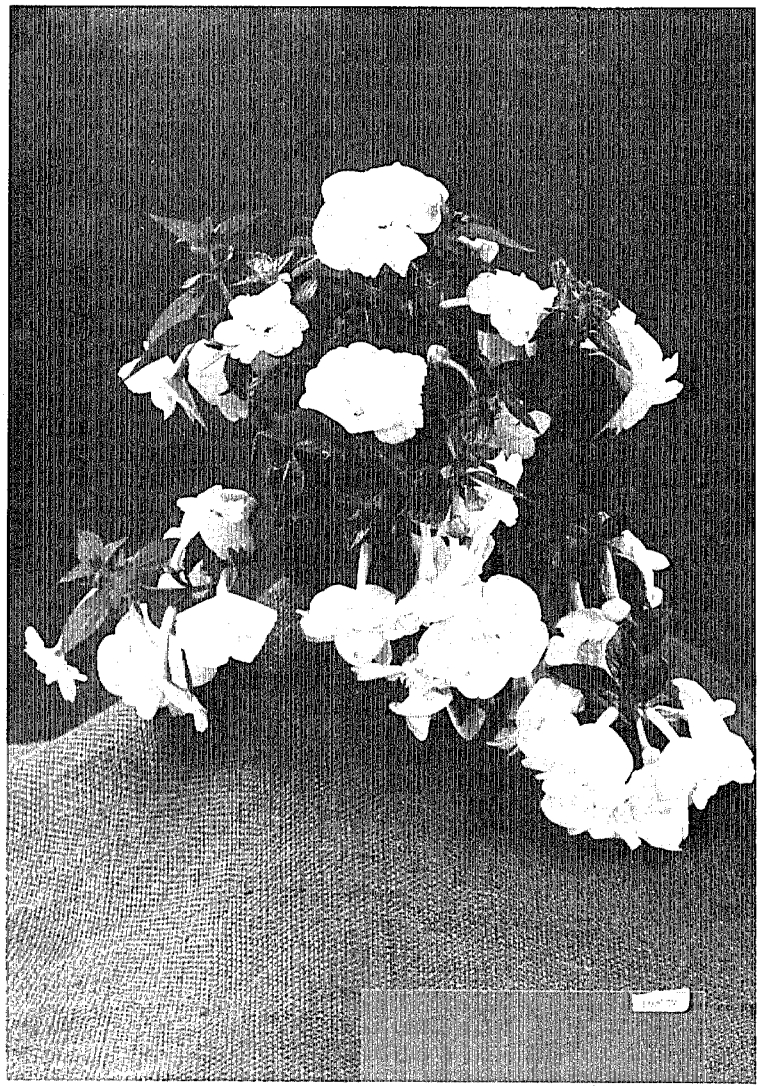

UNITED STATES PATENT AND TRADEMARK OFFICE

CERTIFICATE OF CORRECTION

PATENT NO. : Plant 6,634

DATED : February 28, 1989

INVENTOR(S) : Linda S. Wiles

It is certified that error appears in the above-identified patent and that said Letters Patent is hereby corrected as shown below:

In Column 2, lines 19-22, the final two sentences of the paragraph should read:

> Sheet 1 comprises a greatly enlarged photo of a single flower and surrounding foliage. Sheet 2 is a perspective view of the plant.

Signed and Sealed this

Thirteenth Day of February, 1990

*Attest:*

JEFFREY M. SAMUELS

*Attesting Officer* *Acting Commissioner of Patents and Trademarks*